United States Patent
Haussmann

(10) Patent No.: US 7,512,243 B2
(45) Date of Patent: *Mar. 31, 2009

(54) HEARING PROTECTION EARPLUG WITH A MOVABLE ATTENUATION BUTTON, METHOD FOR MANUFACTURING THE SAME AND USE OF THE SAME

(75) Inventor: Mathias Haussmann, Zurich (CH)

(73) Assignee: Phonak AG, Staefa (CH)

( * ) Notice: Subject to any disclaimer, the term of this patent is extended or adjusted under 35 U.S.C. 154(b) by 619 days.

This patent is subject to a terminal disclaimer.

(21) Appl. No.: 10/925,144

(22) Filed: Aug. 25, 2004

(65) Prior Publication Data

US 2006/0045299 A1 Mar. 2, 2006

(51) Int. Cl.
H04R 25/00 (2006.01)

(52) U.S. Cl. .......................... 381/72; 381/380

(58) Field of Classification Search ............ 381/72, 381/322, 325–326, 328; 181/129–135; 128/867–868
See application file for complete search history.

(56) References Cited

U.S. PATENT DOCUMENTS

| | | | |
|---|---|---|---|
| 2,327,620 A | 8/1943 | Cole | |
| 2,881,759 A | 4/1959 | Hocks et al. | |
| 3,097,643 A | 7/1963 | Santi | |
| 3,702,123 A | 11/1972 | Macken et al. | |
| 4,353,364 A | 10/1982 | Woods | |
| 6,082,485 A * | 7/2000 | Smith | 181/135 |
| 6,148,821 A | 11/2000 | Falco | |
| 6,533,062 B1 | 3/2003 | Widmer et al. | |
| 2003/0133583 A1 | 7/2003 | Widmer et al. | |

FOREIGN PATENT DOCUMENTS

| | | |
|---|---|---|
| AU | 56067/73 | 11/1974 |
| DE | 2 318 735 | 10/1974 |
| DE | 91 12 815.3 U1 | 2/1992 |
| DE | 42 17 043 A1 | 11/1992 |
| DE | 93 13 061.9 U1 | 1/1994 |
| EP | 0 333 298 A1 | 3/1989 |
| WO | WO 00/67638 A1 | 11/2000 |
| WO | WO 02/50499 A2 | 6/2002 |
| WO | WO 02/071794 A1 | 9/2002 |

* cited by examiner

Primary Examiner—Suhan Ni
(74) Attorney, Agent, or Firm—David D. Safran; Roberts Mlotkowski Safran & Cole, P.C.

(57) ABSTRACT

The invention relates to a hearing protection earplug comprising a shell (12) for being worn at least in part in the ear canal of a user, the shell having a sound passage (1016, 1036) extending from an outer sound inlet opening (50) of the shell to an inner sound output opening (1034) adapted to acoustically connect to the user's ear canal, and a noise attenuation button (1002) which is provided at the outer end of the shell, wherein said button is manually movable relative to the shell between a resting position in which the outer sound inlet opening of the shell is closed by the button and at least one communication position in which the outer sound inlet opening of the shell is at least partially opened by the button for enabling sound communication between the environment and the sound passage of the shell, wherein the sound passage (1016, 1036) is designed such that it has a sound attenuation of less than 10 dB averaged over the audible frequencies. The invention also relates to a use of such an earplug and a method for manufacturing such an earplug.

2 Claims, 4 Drawing Sheets

HEARING PROTECTION EARPLUG WITH A MOVABLE ATTENUATION BUTTON, METHOD FOR MANUFACTURING THE SAME AND USE OF THE SAME

BACKGROUND OF THE INVENTION

1. Field of the Invention

The present invention relates to a hearing protective earplug according to the preamble of claim 1 and to a corresponding manufacturing method.

2. Description of Related Art

A large part of the population is exposed to hazardous noise from time to time. This can be at work, whilst traveling, during leisure activities or at home. The exposure can lead to permanent hearing loss, distract people's attention from other hazards or simply cause stress. In order to prevent both accidents and permanent hearing damage, hearing protection devices (HPDs) have been provided in many styles and over many years. It started with the earmuff which is still very relevant and addresses very noisy environments (e.g. airports, construction, shooting) or complex working/communication situations (e.g. fighter pilots). Over the years development of biocompatible soft materials has enabled soft earplugs in different styles and colors as well as recent development of "one fits many" standard semi-soft earplugs in silicon-rubber type materials. For severe situations even the combination of an earmuff and an "in-the-ear" HPD is required to achieve desired attenuation. The physical limitation of hearing protection based on ear worn devices is defined where bone-conduction (body acoustics) becomes dominant at around 40 dB attenuation.

A common disadvantage of the above mentioned HPD styles is wearing discomfort. In case of the earmuffs, they are large which creates difficulties in combination with other head worn gear and they "close off" the ear too much for most applications. The in-the-ear styles mentioned are devices made to fit "the average" ear in one way or the other. Either the fit is provided by softness of the material which leads to undefined device insertion and undefined attenuation, or the fit is provided by standard shaped structures intended to block off the ear canal. In both cases the flat distribution of the individual shape of the outer ear and the ear canal leads to bad fit, pressure points in the ear and undefined positioning of the device.

To address this wearing comfort issue, in-the-ear hearing aid technology has been applied making customized ear molds with passive acoustical filter. These are long lasting devices with good wearing comfort. However, this customization process is traditionally a very manual process creating varying results over time, low reproducibility and the quality is very operator skill dependent.

The idea to use rapid prototyping technology, such as layer-by-layer laser sintering, in manufacturing shells, primarily for hearing aids, is described, for example, in U.S. Pat. No. 6,533,062 B1 or U.S. 2003/0133583 A1.

Environmental sounds are typically comprised of a mixture of various sound wave frequencies having varying intensities. It is well documented that repeated or prolonged exposure to sounds of sufficiently high sound pressure level will cause temporary or permanent hearing loss, i.e. can damage the auditory organ and cause serious hearing problems, including deafness. Harmful noise such as caused by explosions or bursts are often comprised of a mixture of sound wave frequencies of varying intensity. These disturbing frequencies are in both the high and low frequency bands and have an intensity sufficient to cause hearing problems. Individuals who are frequently exposed to such disturbing and sometimes dangerous frequencies and intensities run the risk of incurring such injuries as hearing loss or even deafness. These individuals include workers at demolition or construction sites, operators of heavy, noisy equipment and those in active military service. Ear (i.e. hearing) protection is needed to prevent a loss in hearing acuity and the gradual increase in the threshold of hearing resulting from extended exposures to loud noise.

In general, higher sound attenuation of a hearing protection device will reduce the communication ability with the surroundings. The attempts of the prior art to solve this problem, namely to configure the frequency selective sound attenuation such as to retain a high dynamic in speech or voice frequencies, have failed because of the stringent requirements set up by the high noise concentration at certain working places and in the military area, for example, and the worker, employee or soldier must remove the hearing protection device if he wants to hear a person who wants to communicate with him.

Furthermore, personal communication in high noise fields is a major problem for wearers of HPDs when they are occupied in environments with changing sound or noise amplitude. In such situations, it is highly desired to adapt the hearing protection to the actual noise in terms of amplitude, not primarily in terms of noise frequency. In these cases, the user should change his hearing protection device against another one with higher or lower damping ability. This is complicated since there is a necessity to store a number of different HPDs. Moreover, these different HPDs must not only be provided as such but also, due to hygienic reasons, this number of different HPDs must be provided separately for each person to be admitted to the noisy area concerned.

U.S. Pat. No. 6,148,821 discloses a selective non-linear attenuating earplug according to the preamble of claim 1, in which the button comprises a hollow stem which is inserted into a mating cylindrical outer opening of the shell. The hollow stem and the cylindrical wall of the outer opening of the shell both have a radially extending hole, which may be aligned by rotating the stem relative to the shell. The distal end of the hollow stem is provided with a sound attenuation filter connecting the interior of the hollow stem with a sound bore within said shell communicating with the user's ear canal. When the two holes are aligned, sound may enter through the opening into the interior of the hollow stem, pass through the filter and reach, attenuated by the filter, the ear canal.

However, this approach does not allow non-attenuated sound communication and lacks convenient and safe operation by the user, since the button has to be reset manually and the button has to be rotated.

It is an object of the invention to provide for a hearing protection earplug which is operable to provide temporarily for a full sound communication and which is convenient and safe to handle. It is a further object to provide for a corresponding manufacturing method.

SUMMARY OF THE INVENTION

These objects are attained according to the present invention by hearing, protection earplugs as defined in claims 1, 4, and 29, respectively and by manufacturing methods as defined in claims 35, 36 and 37, respectively.

The solution according to claims 1 and 35 is beneficial in that, by designing the sound passage such that it has a sound attenuation of less than 10 dB averaged over the audible frequencies, non-attenuated or at least close to non-attenuated sound communication, can be achieved in the communication position of the button.

The solution according to claims 4 and 36 is beneficial in that, by providing means for biasing the button towards the resting position, manual operation of the button is convenient, since it automatically returns to the attenuation position, thereby avoiding the danger that the user button forgets to return the button to the attenuation position before being exposed to noise which may damage the user's hearing.

The solution according to claims 29 and 37 is beneficial in that, by providing the movement of the button between the resting position and the communication position as an axial movement, convenient handling of the button, for example by simply pressing the button for achieving the communication position, is enabled.

These and further objects, features and advantages of the present invention will become apparent from the following description when taken in connection with the accompanying drawings which, for purposes of illustration only, show several embodiments in accordance with the present invention.

The devices shown in the figures are represented in an enlarged scale. Furthermore, the different parts of the devices are also not necessarily at scale.

Figure 1:
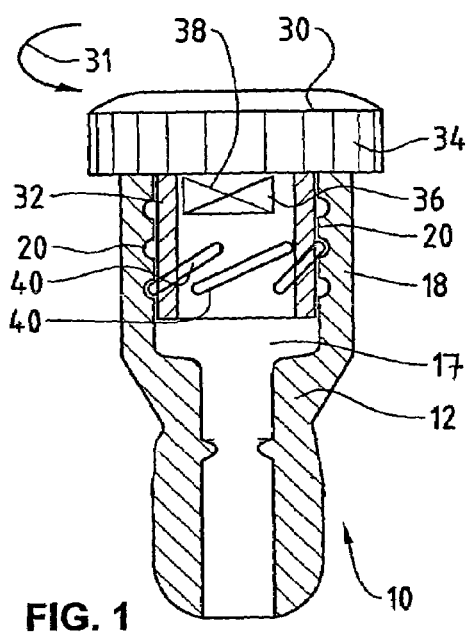
FIG. 1 shows a partly axially sectioned side view of an outer portion of a passive hearing protection earplug according to a first embodiment of the invention, the attenuation button being in an attenuation position.
Figure 2:
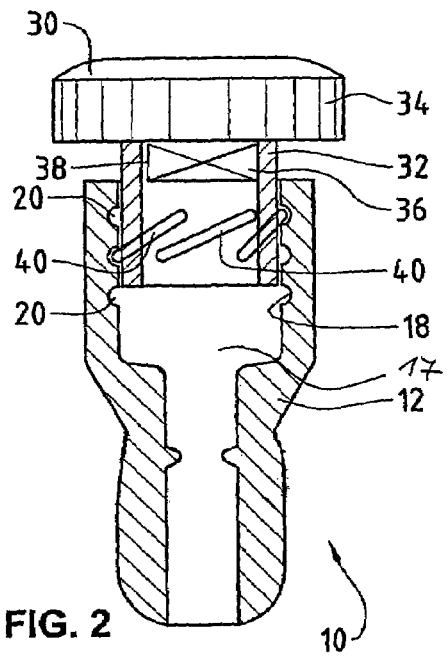
FIG. 2 shows a view like FIG. 1, with the attenuation button being shown in a communication position.

The HPD of FIGS. 1 and 2, is a passive hearing protection earplug 10 which comprises a hollow shell 12 to be introduced into the auditory canal of an ear.

The cylindrical inner wall of an outer, cylindrical and hollow portion 18 of the shell 12 has a number of partial turns 20 of a relatively steep female thread cut as grooves into the wall of this cylindrical portion.

A button 30 is inserted from above into the outer cylindrical portion 18 of the shell 12. The button 30 is provided with reeding so that it may better be actuated by hand. The button 30 comprises a disk like top portion 34 and a downward directed, hollow cylindrical, integrally formed sleeve-like portion 32. This sleeve 32 has a rectangular triangle cut-out 36; the long leg of the triangle 36 being parallel to the upper end plane of the cylindrical portion 18 or to the lower surface of the top portion 34 of the button 30. The corner of the triangle formed by the short leg and the hypotenuse touches the lower surface of the top portion 34 of the button 30.

A second triangular cut-out 38, drawn in dotted lines, may be provided on the diametrically opposed side of the sleeve 32.

Outer ribs 40 that are inclined to the horizontal plane in FIGS. 1 and 2 form a steep multiple male thread. These ribs 40 are engaged into the grooves 20 of the shell 12. The first assembly of the device is possible thanks to the resilience of the material that yields when the button 30 is forced from above into the outer portion 18 of the shell 12.

As it can be seen by comparing FIGS. 1 and 2, the attenuating action of the earplug is at a maximum when it is in the position shown in FIG. 1, with the button 30 being in a sound attenuation position in which it closes the sound inlet opening formed by the open outer end of the portion 18 of the shell 12. When the button 30 is turned counterclockwise, i.e. in the direction of arrow 31, into the open position shown in FIG. 2, the cut-out 36 is gradually opened when the button 30 rotates and simultaneously raises from its attenuation position, and in the open (and elevated) position the attenuation is at a minimum, thereby achieving a communication position in which the sound inlet opening of the outer portion 18 of the shell is released from the button 30. The two positions of the button differ from each other by an angle of rotation of from about 40° to about 120°, preferably of about 70 to 100°, depending on the size of the cut-out 36.

The shell 12 comprises an sound passage 17 which extends from the sound inlet opening, i.e. the open outer end of the outer portion 18 of the shell 12, to an inner sound output opening 14 at the distal end of the shell 12 communicating with the user's ear canal. In order to achieve unobstructed or at least almost unobstructed sound communication in the communication position of the button 30, the minimum cross section of the sound passage 17 should be an area corresponding to the area of a circle having a diameter of 0.5 mm.

Figure 3:
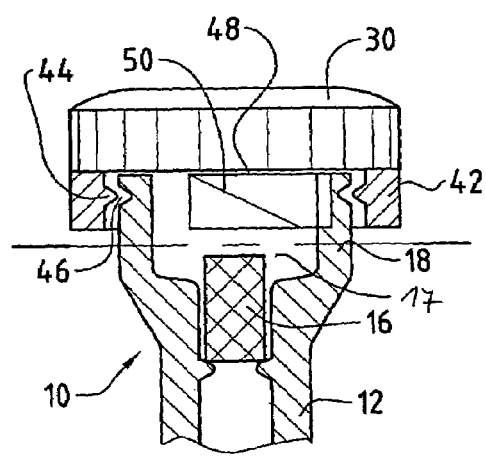
FIG. 3 shows a view like FIG. 2, with a second embodiment of the invention being shown.

FIG. 3 shows a second embodiment of the invention. Similar parts as in FIGS. 1 and 2 bear the same reference signs. The button 30 has a downward projecting, ring-like rim 42 that receives the outer portion 18 of the shell 12. A circular rib 44 at the cylindrical inside of the rim 42 engages into a circular groove 46 of the outer portion 18 of the shell 12. (The locations of groove 44 and rib 46 may of course be interchanged.) The rim 42 has one or more rectangular cut-outs 48 that are each opposed to one or more triangular cut-outs 50, shown in dotted lines, in the wall of the outer portion 18 of the shell 12. The sound passage 17 may comprise a passive acoustic attenuation filter 16.

When the button 30 is rotated with respect to the shell 12, in the clockwise direction in FIG. 3, the rectangular cut-out 48 will first open a small triangular portion of the cut-out 50. Then, when rotation is continued, the rectangle 48 will finally completely cover the triangle 50, and in this position, the maximal opening of the device is achieved.

Figure 4:
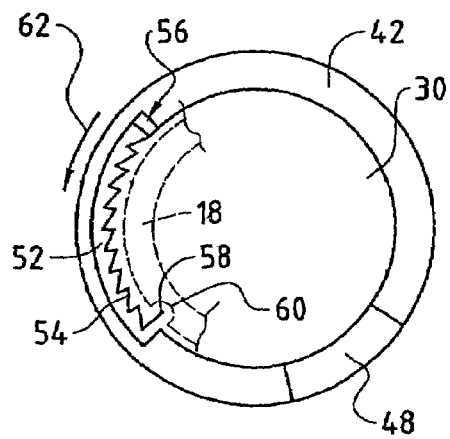
FIG. 4 shows a partially sectioned plan view of the button of the embodiment of FIG. 3.

FIG. 4 shows an example of how to bias the button 30 of FIG. 3 towards the attenuation position. The rim 42 of the button 30 comprises an annular groove 52 in which a helicoidal spring 54 is lodged. In FIG. 4, this spring is shown as a pressure spring. At one end 56, the spring 54 is fixed to the inner surface of the groove 52. The other end 58 of the spring 54 is bent radially inwards and enters into an axially groove 60 in the outer cylindrical surface of the outer cylindrical portion 18 of the shell 12.

FIG. 4 shows the attenuation position of the device. When the button 30 is now rotated in direction of the arrow 62, which means into the open position, the spring 54 will be compressed. In the open position, the button must be retained by hand against the force of the spring 54. In this position, speech communication between two persons, close to one another, is facilitated. When this direct communication is no longer needed, the button 30 is released, and this button will be rotated by the spring 54 into its closed (or silent) position. In this way, the wearer of the device will not need to manually turn the button back into the attenuation position.

Of course, the one skilled in the art will be aware that the pressure spring 54 may also be replaced by a tension spring and he will adapt the construction accordingly.

In both embodiments described above, the movement of the button 30 against the shell 12 may be limited by stop means known per se and not shown.

In the embodiments shown and described, the area of the opening provided by rotating the button 30 is essentially linearly proportional to the angle of rotation. However, in order to adapt the varying attenuation obtained by the device to the approximately logarithmic sensibility of the ear to noise intensity, the straight borders of the openings 36, 38, 48, 50 may be replaced by appropriately curved ones.

The device of this invention may be varied in several ways. In a manner known per se, the shape of the device or earplug may be adapted to the shape of the human auditory canal and/or the auricle. The device of this invention may be equipped with a cord, also known per se, for avoiding its loss. The position of the button may be indicated by marks so that it can be seen by another person.

The advantages of the invention are multiple. Thus, the handling of the button is easy and can also be effected with dirty finger or with gloved hands. The button cannot be lost. The device has a pleasant aspect. The device has an extremely wide range of adjustment, between virtually no attenuation until a nearly full attenuation of environmental noise. Furthermore, the embodiment having the reset function diminishes the risk of hearing damages.

The invention is not limited to the embodiment described above. Other constructive solutions may afford equivalent results. Thus, for example, the invention as defined in the independent claim may also be realized when said button is movably held within said plug for an axial displacement wherein the configuration of the opening(s) in the button can also be an equilateral triangle with its summit directed upwardly or any other configuration that provides an increasing passageway in response to the displacement of the button. Such an approach allows a still easier reset movement of the button. Furthermore, the triangular opening in the stem 18 and the rectangular opening in the rim 42 may be interchanged.

Figure 5:
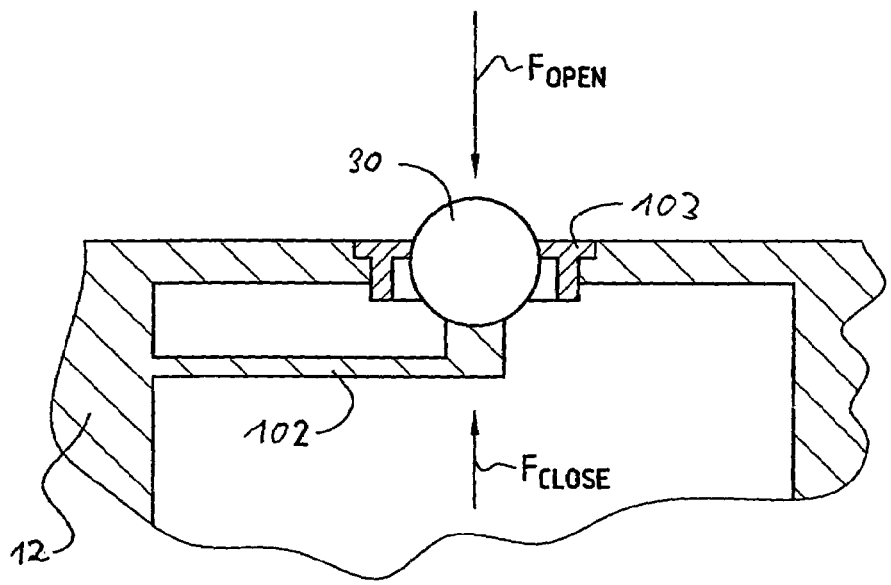
FIG. 5 shows a partially axially sectioned view of the button of a third embodiment of the invention.

FIG. 5 shows an embodiment wherein the attenuation button is formed as a ball 30, i.e. with a spherical shape, which is biased by a spring lever 102 formed integral with the shell 12 outwardly towards an circular opening in an insert part 103 inserted into a sound inlet opening at the outer end of the shell 12 for closing this sound inlet opening in the attenuation position of the ball 30. The communication position is achieved by manually urging the ball 4 inwardly again the bias force provided by the spring lever 102.

The insert part 103 may be replaced by an integral portion of the shell 12.

Figure 6:
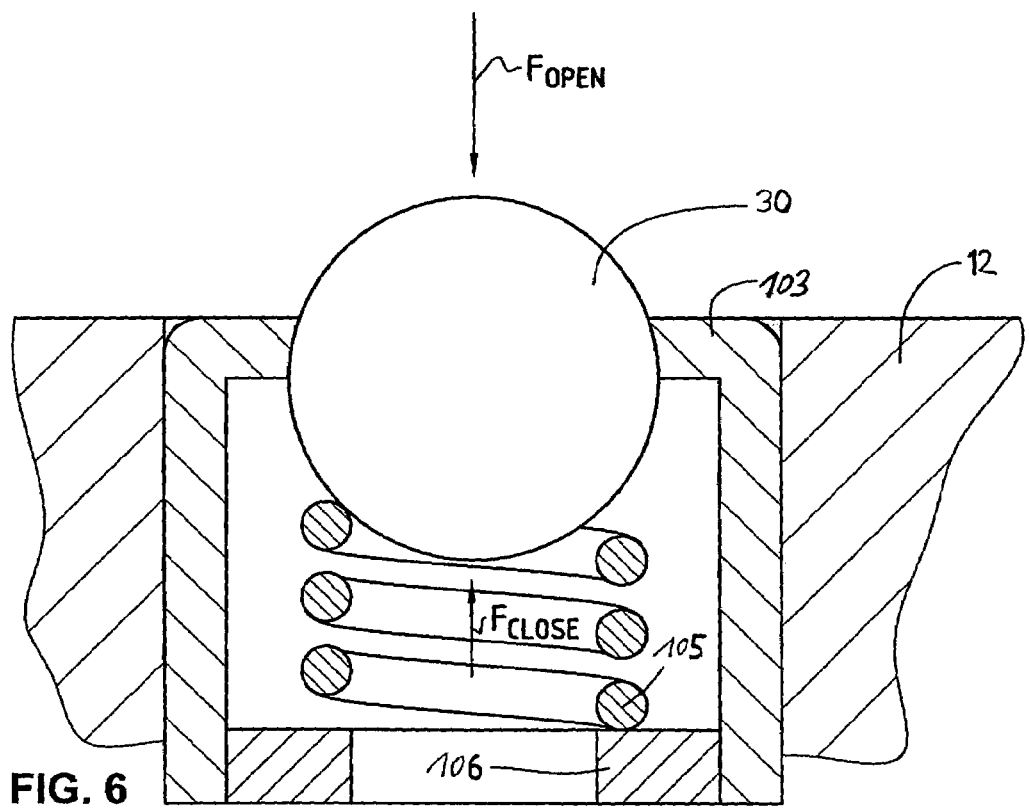
FIG. 6 shows a view like FIG. 5 of the button of a forth embodiment of the invention.
Figure 7:
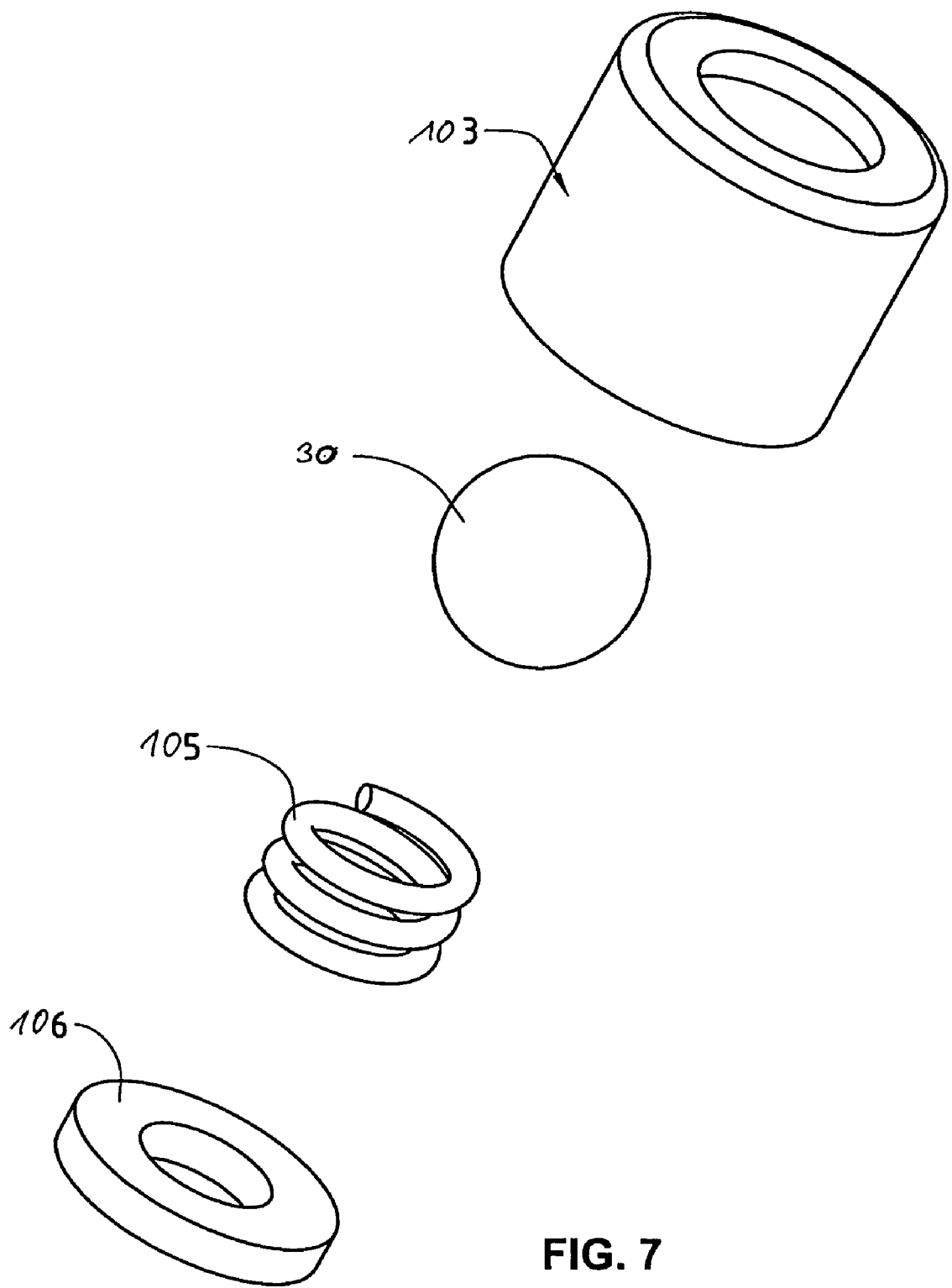
FIG. 7 shows an exploded view of the button of FIG. 6.

FIGS. 6 and 7 show a modified embodiment, wherein the insert part 103 not only acts as a stop for the ball 30 in the attenuation position but in addition serves to support the ball 30 in the communication position. To this end, the insert 103 is provided at its distal end with a retention ring 106 which supports a helical spring 105 biasing the ball 30 outwardly into the attenuation position.

Figure 8:
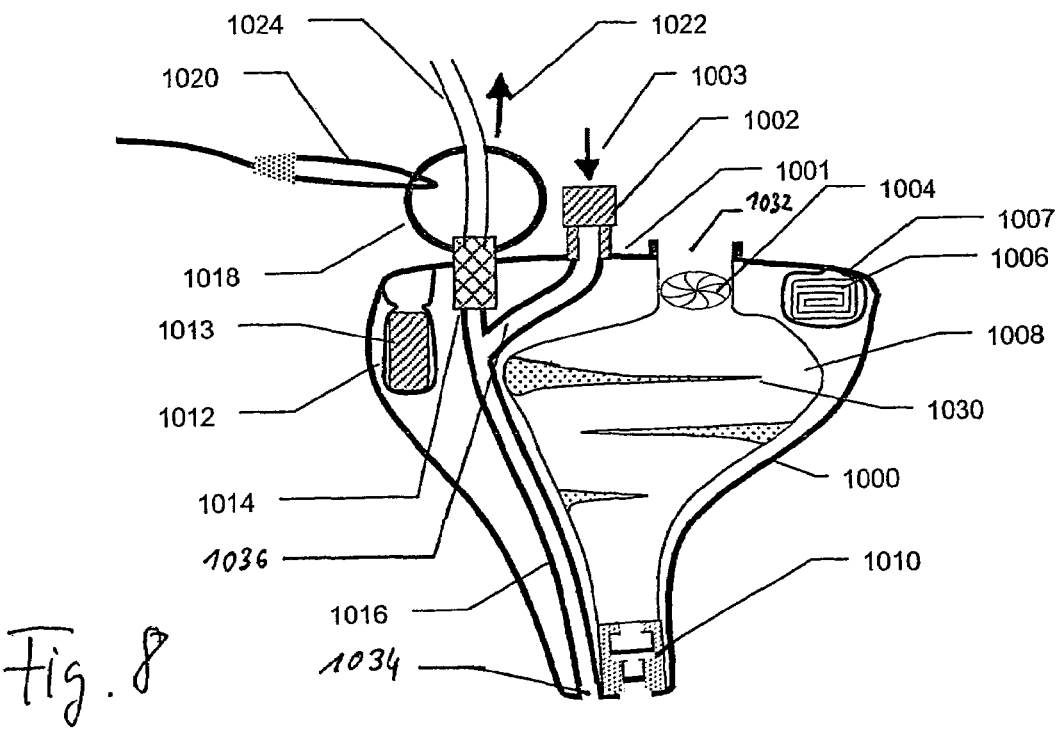
FIG. 8 shows a longitudinal sectional view of an example of a passive hearing protection earplug according to the invention when connected to an external measurement tube.

FIG. 8 shows an example of a customized passive hearing protection earplug with a shell 1000 having a faceplate 1001 as its outer end and having a measuring channel 1016 formed integral with the shell 1000 and extending from a measuring hole with an adapter element 1014 to a sound opening 1034 at the inner (i.e. distal) end of the shell 1000. In FIG. 8, an external measuring tube 1024 is connected to the adapter element 1014 for connecting the measuring channel 1016 with an external acoustic measuring unit for performing in-situ measurements, for example, regarding the actual attenuation achieved by the earplug when worn by the user. The adapter element 1014 is provided with a cord fixation ring 1018 for fixing a neck cord 1020 at the shell 1000. An acoustic attenuation filter 1010 is provided at the inner end of a resonance cavity 1008 extending from a sound input opening 1032 at the faceplate 1001 to the filter 1010.

During normal operation of the earplug the external measuring tube 1024 is removed an the measuring hole is closed by removable plug (not shown) connected to the adapter element 1014 instead of the measuring tube 1024.

At an intermediate point of the measuring channel 1016 a sound passage 1036 merges with the measuring channel 1016. The sound passage 1016 extends to a sound inlet opening in the faceplate 1001 which is provided with a sound attenuation button 1002 operable in the direction 1003 to acoustically open or close the sound inlet opening, preferably by axially pushing the button 1002. The button 1002 preferably is biased towards the attenuation position and may be constructed according to the embodiments of FIGS. 5 to 7. In general, however, the button 1002 also may have a different construction, for example according to the embodiments of FIGS. 1 to 4.

The sound passage 1036 and the measuring channel 1016 preferably have a minimum cross sectional area corresponding to the area of a circle having a diameter of 0.5 mm.

The sound passage 1036, together with the distal part of the measuring tube 1016, serves to acoustically by-pass the attenuation filter 1010 for enabling an unobstructed or almost unobstructed communication function.

Figure 9:
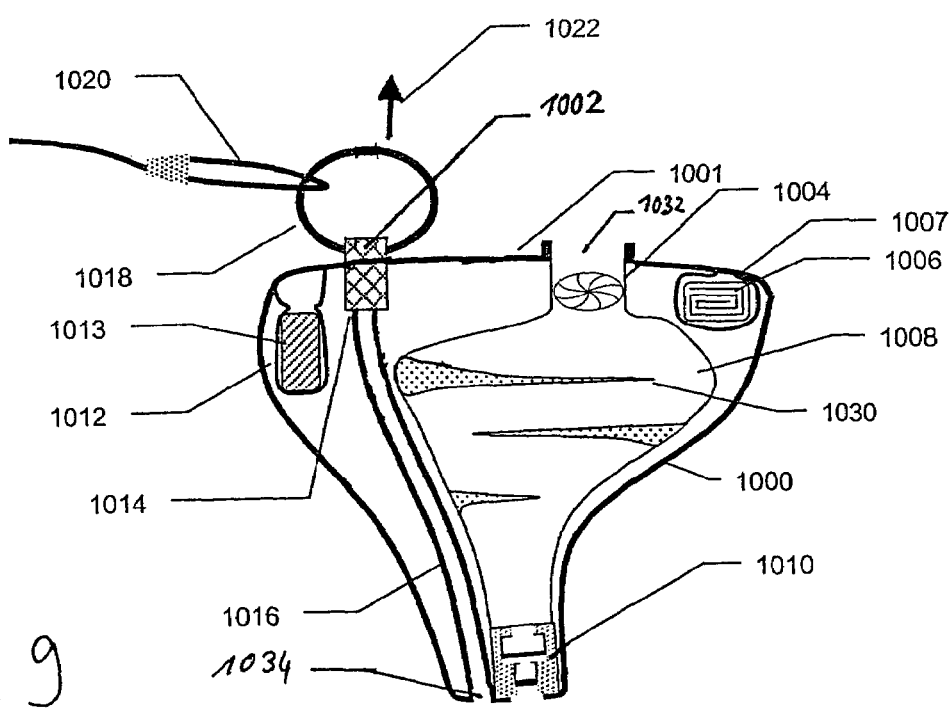
FIG. 9 shows a view like FIG. 8, with a modified embodiment being shown.

FIG. 9 shows a modified embodiment of the earplug of FIG. 8, wherein no separate sound passage 1036 is provided but rather the entire measuring channel 1016 serves to by-pass the attenuation filter 1010 for realizing the communication function. This is achieved by integrating the sound attenuation button 1002 within the plug which is connected to the adapter element 1014 for closing the measuring hole in the normal operation mode of the earplug when no in-situ measurements are performed.

In general, the sound attenuation button is designed to attenuate, in its attenuation position, sound waves reaching the button. This includes the option to provide the attenuation button itself with at least one defined acoustic filter, e.g. a membrane filter, to achieve a defined sound attenuation in the attenuation position. In any case, the button, in its communication position, acts to by-pass such filters.

In general, the sound passage is preferably designed such that it has a sound attenuation of less than 10 dB averaged over the audible frequencies. This can be achieved by selecting the shape and the minimum cross section accordingly, for example by choosing a minimum cross section with an area corresponding to the area of a circle with a diameter of 0.5 mm.

Generally, the shell is preferably a customized hard shell having an elasticity from shore D 85 to shore D 65, for example made of polyamide, and an outer surface individually shaped according to the measured inner shape of the user's outer ear and ear canal. The customized shell may be produced by an additive or incremental build-up process, such as layer-by-layer laser sintering (also known as "selective laser sintering") of a powder material. The inner shape of the user's outer ear and ear canal may be measured, for example, by three dimensional (3D) laser scanning of the ear or by taking an impression of the ear which then undergoes 3D laser scanning. Such manufacturing processes are described for example in U.S. Pat. No. 6,533,062 B1.

In particular, fabricating the shell by selective laser sintering includes the option to fabricate also the attenuation button including all components, e.g. the biasing spring, together and simultaneously with the shell in a single process step, whereby the usually required step for mounting the button at the shell is eliminated. In other words, by selective laser sintering the button may be fabricated already at its final place at the shell.

FIGS. 8 and 9 show examples of a passive hearing protection earplugs, wherein some additional features are combined which may be advantageously implemented by manufacturing the shell of the earplug by an additive build-up process, such as layer-by-layer laser sintering.

The sound input opening 1032 is provided with a mechanical peak clipper 1004. The resonance cavity 1008 is provided with an inner mechanical structure 1030 for frequency tuning. An insert cavity 1007 for a RFID (radio frequency identification device)-tag 1006 and an insert cavity 1012 for a detectable metal part 1013 are formed integral with the shell 1000. While the neck cord 1020 serves to prevent loss of the earplug, the ring 1018 or the cord 1020 also may serve to manually pull the earplug in the axial direction 1022.

In the following these additional features and their functions will be explained in more detail.

Semi-Integrated Passive Filter

In passive HPDs acoustical filters mainly serve two purposes: firstly there is the defined amount of attenuation, secondly the filter can shape the frequency response of the attenuation in order to protect some frequencies while letting others through (e.g. block low frequency noise and let speech pass above 1 kHz). The proposed base technology enables both usages of predefined component placement geometries (e.g. cavities 1012 for metal component 1013 insertion) as well as semi-integration of functions where the material itself becomes part of the solution (e.g. insert cavities, acoustical filters). The semi-integrated passive filter 1010 is a structure of the second kind, where the tubes are made in shell material while the membranes are inserted components. Selection of membranes can be done to order and individual need, hence the component remains customizable. The filter must be considered and dimensioned together with other filter means like the customizable front chamber shaping structure (or resonance cavity) 1008, 1030 (Helmholtz resonator) and the mechanical peak clipper 1004.

Inverse Anatomy Force Button

A further level of integration of a communication on/off switch is based on the shell technology combined with the natural anatomy of the outer ear. In addition to a defined audio "leak" via a tube 1016 through the HPD, there is the alternative of creating a temporary leak between the device and the outer ear by slightly pulling the device out of the ear. This pull can be done by the cord 1020 or directly by grip and pull on the cord ring 1018. If the shell 1000 is shaped in an appropriate manner, the ear shape is such that the device will be naturally pulled back in place when the pull is relaxed.

Intelligent Passive HPD

Inserting a device into the ear principally blocks the acoustical tube (ear canal) and destroys the natural outer ear amplification and frequency shaping (open ear gain, OEG). The open ear has a natural resonance in the frequency area of the most critical speech information, hence this loss is a real loss and not normally desired. The resonance frequency is given by the length of the tube; hence there is a need for compensation of the reduced length. This can be individually modeled and implemented with a defined acoustical front (outer) chamber 1008 and artificially stretched to a desired length by a mechanical means 1030 for resonance shaping directly integrated into the shell making process, possibly in combination with frequency shaping filter 1010 and means for maximum power limiting such as a mechanical peak clipper 1004.

Mechanical Peak Clipping

Many applications for HPDs experience strong variations in noise exposure over time. The extreme example is people shooting with guns (military, hunters) where speech communication in-between the actions is strongly desired and where the sound gets very loud for a short time. In active devices such conditions have been solved with so-called "peak clippers" which are fairly easy to implement in electronics and which limit the output of the device independent of the input signal while leaving the signal undistorted for normal noise levels. For a passive device this can be realized by a pressure sensitive valve 1004 opening or blocking the audio canal at the sound inlet.

Detectable HPD

HPDs are mostly used in industrial environments. In the food processing industry an additional requirement also affects these devices. Any foreign particle (to the food ingredients) must be detectable within the production process. For HPDs this implies that the devices need to contain a certain amount of metal to enable the detection equipment to find it if lost in the production line. Metal can be inserted into HPDs in a number of different ways: metal can be mixed into the shell base material 1000, a specific metal component 1013 can be mounted in a prepared cavity 1012, the cord adapter faceplate element 1014 can be made of metal and the button part of the on/off switch 1002 can be made of metal. In a HPD with a RFID tag, the tag itself is detectable if the equipment for detection is implemented in the production line.

HPD Wearing Compliance

Wearing of HPDs in industrial environments obliges to regulations in most countries. Assuming that the devices have the desired protective effect when they are worn (most other topics described address this very issue), the wearing itself becomes the compliance control topic. With recent developments in miniaturized RFID (radio frequency identification devices) technology, it becomes feasible to implement such devices into a customized HPD given the shell technology described. The RFID tag 1006 is inserted into a predefined cavity 1007 and when the wearer passes through gateways equipped with RFID detection systems, the positions of the two HPDs can be obtained and the control function carried out according to whether a predefined condition regarding the detected positions is fulfilled or not (e.g. separation of the HPDs according to the width of the head and height of the HPDs according to the ear height). As mentioned, the RFIDs can also serve as HPD detection devices in food production processes.

Basic Functions

Functions that conventionally are mounted components, such as a grip handle for insertion and removal of the HPD, can easily be integrated with use of the shell technology. The product design and assembly more and more becomes a software issue and the individual product is increasingly designed to order according to the specific requirements of each customer.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. Hearing protection earplug comprising a shell for being worn at least in part in an ear canal of a user, said shell having a sound passage extending from an outer sound inlet opening of said shell to an inner sound output opening adapted to acoustically connect to said user's ear canal, and a noise attenuation button which is provided at an outer end of said shell, wherein said button is manually movable relative to said shell axially between a resting position in which said outer sound inlet opening of said shell is closed by said button and at least one communication position in which said outer sound inlet opening of said shell is at least partially opened by said button for sound communication between an environment and said sound passage of said shell, further comprising means for axially biasing said button towards said resting position, said biasing means comprising a spring seated at said shell and at said button.

2. Hearing protection earplug according to claim 1, wherein said shell contains an acoustic filter for one of axially dividing said sound passage and forming one end of said sound passage.

* * * * *